United States Patent [19]

Larro

[11] 4,188,265
[45] Feb. 12, 1980

[54] PORTABLE INCUBATOR

[75] Inventor: Harold D. Larro, Tigard, Oreg.

[73] Assignee: Almore International, Inc., Beaverton, Oreg.

[21] Appl. No.: 877,921

[22] Filed: Feb. 15, 1978

[51] Int. Cl.² ............................................. C12K 1/10
[52] U.S. Cl. ................................. 435/313; 435/80 G
[58] Field of Search ................................ 195/127, 139

[56] References Cited

U.S. PATENT DOCUMENTS

| 2,463,143 | 3/1949 | Brewer | 195/127 |
|---|---|---|---|
| 3,483,089 | 12/1969 | Brewer | 195/127 |
| 3,562,114 | 2/1971 | Steidl et al. | 195/139 |
| 4,033,826 | 7/1977 | Larsen et al. | 195/139 |

Primary Examiner—Alvin I. Tanenholtz
Assistant Examiner—Robert J. Warden
Attorney, Agent, or Firm—Townsend and Townsend

[57] ABSTRACT

A portable incubator having an open top jar which is closed by a lid secured to the jar by a releasable clamp. The lid has a conduit on its upper surface, the conduit communicating with a hole through the lid and provided with a pair of opposed ends. There is a valve for each end of the conduit, respectively. A holder for culture dishes can be moved into and out of the jar, the holder being formed by a number of rigid straps arranged to form a side opening in the holder so that the culture dishes can be put into the holder and supported on the bottom of the same. A hand-held, hand-actuated vacuum pump can be carried with the jar and has a flexible tube connecting it to one end of the conduit so that the interior of the jar can be evacuated in a short time. The opposite end of the conduit is adapted to permit a gas to be injected into the jar under pressure after the jar has been evacuated. The jar can be placed in an operative position in a housing having a top wall provided with an opening for receiving the jar. A flange on the upper end of the jar engages the top wall to limit the inward travel of the jar into the housing. In one form of the invention, heater means is provided on the inner surface of the housing. In another form, a cylinder extending downwardly from the opening in the top wall is adapted to receive the jar and has a heater coil surrounding it.

16 Claims, 6 Drawing Figures

PORTABLE INCUBATOR

This invention relates to improvements in incubators and, more particularly, to a portable incubator which can be moved from place to place and evacuated with a hand-held vacuum pump.

BACKGROUND OF THE INVENTION

In growing cultures in incubator jars, it has been the customary practice to place the jar under positive pressure by means of a gas, either generated from a pellet or being provided in a flow-through process, which displaces the air or eliminates oxygen in the jar to thereby promote the growth of the cultures. Because of these practices, a dangerous pressure build-up could occur in the jar which might break the jar or force the lid off the jar. Some attempts have been made to evacuate the jar but these have been not too successful and require a laboratory vacuum pump which is permanently installed.

Prior art references pertinent to this subject are the following U.S. Pat. Nos. 2,463,143, 3,483,089 and 3,562,114. A reference from a periodical is also pertinent, this reference being entitled "An Anaerobic Culturing And Sampling Apparatus", Canadian Journal of Microbiology, Vol. 11, Pages 597 and 598 (1965).

None of the patents or the reference shows or suggests a simple incubation apparatus which is portable and which uses negative pressure at all times during operation. While U.S. Pat. No. 3,562,114 and the above periodical reference mention the use of vacuum, they do not teach or suggest a simple and expeditious manner of providing a culture jar which can be quickly and easily evacuated but suggest such a jar which depends upon a cumbersome, permanently installed vacuum system.

SUMMARY OF THE INVENTION

The present invention provides an improved incubator which can be hand carried from place to place and used under negative operating pressures at all times. To thie end, the portable incubator of this invention comprises a jar having an open top for receiving a culture dish holder. A lid is clamped to the top of the jar for closing the same, the jar having a seal for engaging the lower surface of the lid near its outer periphery. A conduit carried by the lid near the upper surface thereof communicates with the interior of the jar when the lid is secured to it. The conduit has a pair of opposed, open ends, there being a valve for each end, respectively, for controlling the flow of fluid through the conduit.

A hand-held, hand-actuated vacuum pump capable of being carried with the jar, is coupled to one end of the conduit on the lid for evacuating the jar after the holder with one or more culture dishes has been inserted into the jar. After evacuation of the jar, a gas can be directed into the jar yet the resulting gas pressure in the jar will be negative to avoid pressure build-up problems associated with the prior art as mentioned above.

The jar can be placed in a box-like housing having a top wall provided with an opening for receiving the jar. A flange on the upper end of the jar limits the inward travel of the jar into the housing and supports the jar in an operative position. The housing has heater coil means on the sidewall or bottom wall thereof for heating the contents of the jar when the jar is in its operative position. In an alternate embodiment, the housing has a cylinder extending downwardly from the top wall for receiving the jar, the cylinder being of heat conductive material and provided with a heater coil carried by and surrounding its outer surface. The latter embodiment provides better heat distribution within the jar and eliminates any electrical shock hazards which might arise by a person inserting a hand into the housing.

The portable incubator of this invention combines versatility, safety and economy with absolute integrity in culture growth. The incubator does not use gas-generating pellets or flow-through gas methods which can be time consuming, costly and inaccurate. Instead, the incubator of this invention simply operates on a vacuum principle with an introduction of gas into a closed, evacuated system to maintain the highest atmospheric quality.

The jar of the incubator can be purged of all air and its natural impurities in a few minutes. This provides a standard for reliability and reduces culture mortality. The result is greater culture retrievability of even the most fastidious organisms. Anerobic cultures are exposed to normal atmosphere for only a few moments in contrast to the gas-generating pellet system of the prior art.

Because the incubator of the present invention is a closed system, gas is not wasted in comparison to flow-through gas systems of the prior art. Only the necessary amount of gas is injected to create the desired atmosphere in the jar. Thus, gas consumption is greatly reduced. In addition, large gas cylinders are not necessary since a certified gas mixture (oxygen-free) is readily available in mini-cylinders which save space and reduce costs.

Gas generating pellets are considerably more costly to use in comparison with the use of the incubating unit of the present invention, especially when multiple openings of the culture jar are required. Each time the jar is opened, a new gas-generating pellet must be used to keep the desired environment. The present invention greatly reduces the cost per jar opening over the gas generating pellet systems.

The incubator of the present invention is completely portable and small for use in an office. It is also easily adapted for use in commercial labs and hospitals.

The primary object of the present invention is to provide an improved incubator unit for culture dishes, wherein the incubator is completely portable, uses negative pressures in the culture dish jar at all times, is provided with a device for evacuating the section notwithstanding the fact that the jar and the device can be carried together as a unit from place to place.

Another object of the present invention is to provide a portable incubator of the type described wherein the jar can be placed in a housing having means either on the inner surface of the housing wall or on the outer surface of a cylinder extending into the housing for receiving the jar so that heat can be applied to the contents of the jar to provide the desired environment for culture growth therewithin.

Other objects of this invention will become apparent as the following specification progresses, reference being had to the accompanying drawings for an illustration of the invention.

IN THE DRAWINGS

Figure 1:
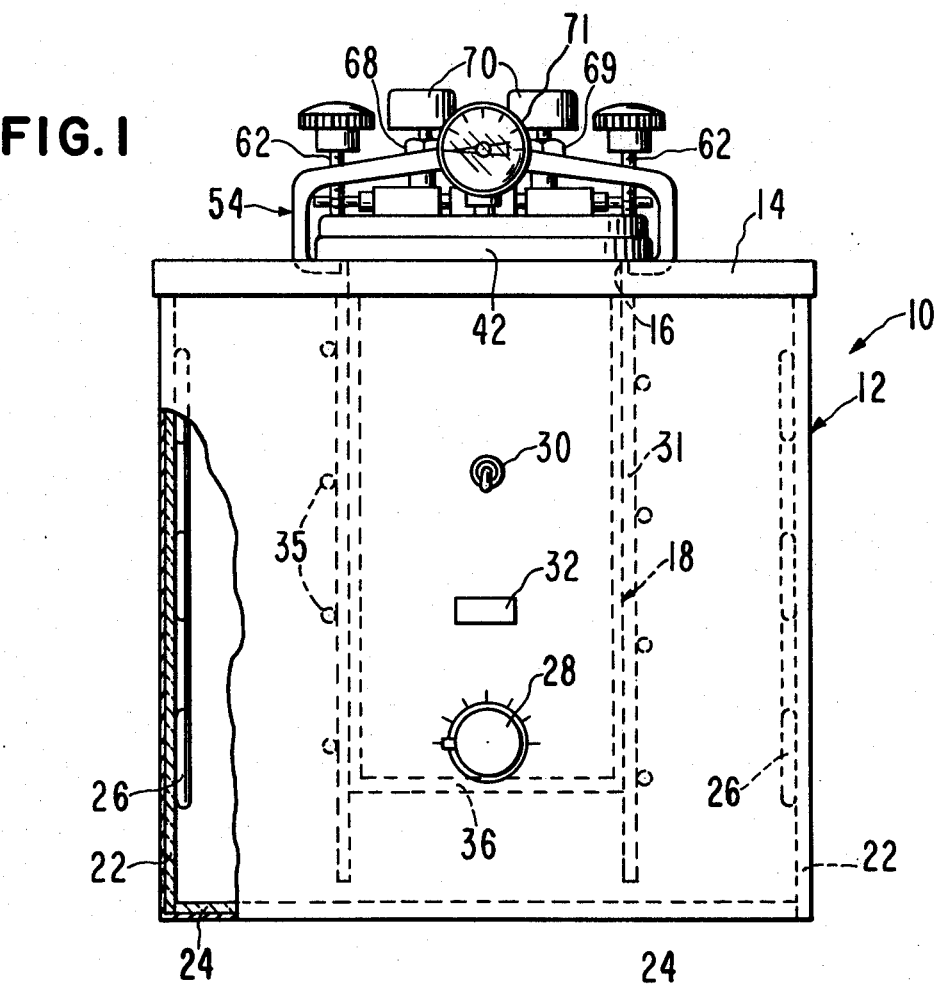
FIG. 1 is a side elevational view, partly broken away and in section of the portable incubator apparatus of this invention.

The portable incubation apparatus of the present invention is broadly denoted by the numeral 10 and includes an incubation jar 18 (FIG. 3) which is adapted for receiving a number of stacked culture dishes 20. Jar 18 can be used with or without a housing 12 provided with a top wall 14 having an opening 16 (FIG. 2) therein, for receiving the jar.

Figure 2:
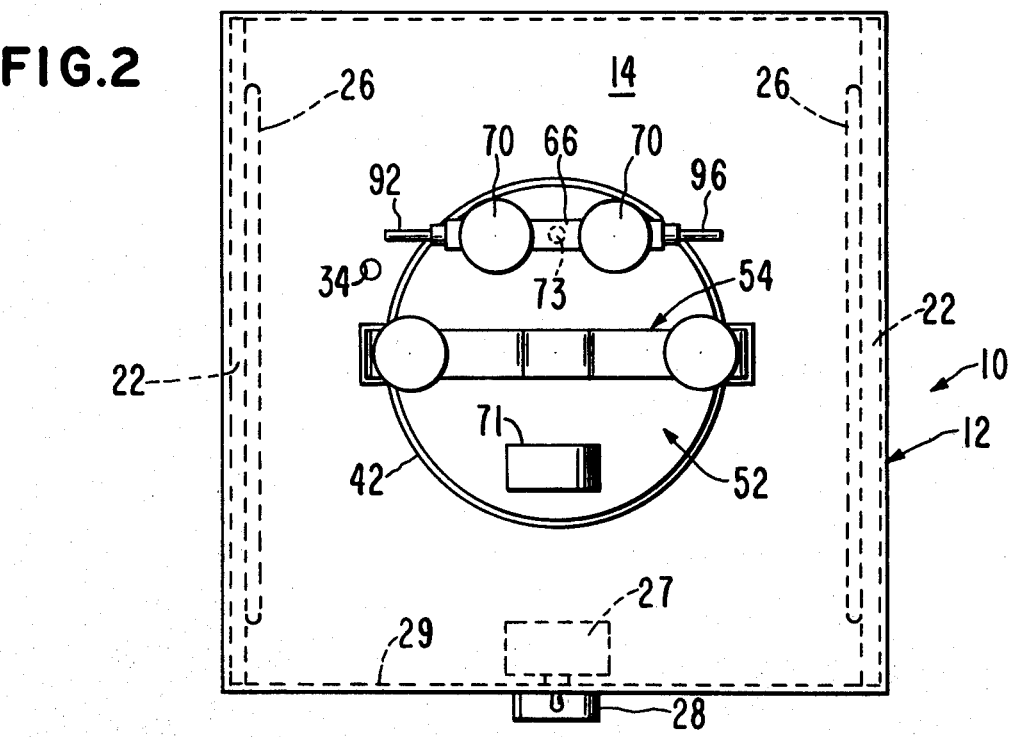
FIG. 2 is a top plan view of the apparatus.

Housing 12 can be of any shape and size but typically it has four sides 22 extending upwardly from a bottom 24 adapted to rest on a support surface, such as a laboratory table. A pair of opposed, parallel sides 22 have respective heating coils 26 on the inner surface thereof as shown in FIGS. 1 and 2 for heating the interior of the housing when jar 18 is in the operative position shown in FIG. 1. Heating coils 26 are coupled to a source of powers such as 110 volts A.C. A temperature control 27 (FIG. 2) operated by a rotatable knob 28 (FIG. 1) is mounted on another sidewall 29 of the housing for controlling the current flow to the coils and thereby controlling the temperature in the housing. A power switch 30 is mounted on the housing above knob 28, there being a pilot light 32 below switch 30 to indicate when electrical current is being directed through coils 26. A thermometer can be inserted into a hole 34 (FIG. 2) in top 14 of housing 12 to indicate the temperature within the housing.

In an alternate embodiment, an open-ended sleeve or cylinder 31 (shown in dashed lines in FIG. 1) is secured at its upper open-end to top wall 14 of housing 12 so as to extend downwardly from opening 16 to top wall 14. Cylinder 31 is adapted for receiving jar 18 and has an open lower end which terminates near or at bottom 24, the cylinder surrounding the jar when the latter is in its operative position shown in FIG. 1. A coil heater 35 surrounds cylinder 31 to heat the contents of jar 18. Thus, when cylinder 31 is used, heating coils 26 are not needed. Heater 35 gives better heat distribution to the contents of jar 18 and eliminates hazards due to electrical shock, such as if a person were to place a hand in housing 12 through opening 16 and touch the wires of heating coils 26. Cylinder 31, if used, is permanently attached to top wall 14.

Figure 6:
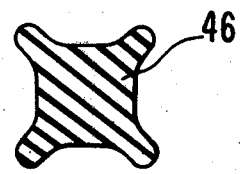
FIG. 6 is an enlarged cross-section of the seal between the jar and the lid.

Jar 18 is typically transparent and is made of any suitable material such as a suitable plastic capable of conducting heat. The jar has a bottom 36 (FIG. 3), a cylindrical sidewall 38 and an open top 40 (FIG. 4) surrounded by an annular flange 42 provided with a groove 44 having a quad seal 46 therewithin, seal 46 having an uncompressed cross-section shown in FIG. 6 so that, when the seal is compressed as shown in FIG. 4, it will provide a substantially perfect seal between flange 42 and an annular, outer peripheral face 48 in the bottom surface 50 of a lid 52 used to cover the open top 40 of jar 18.

Figure 4:
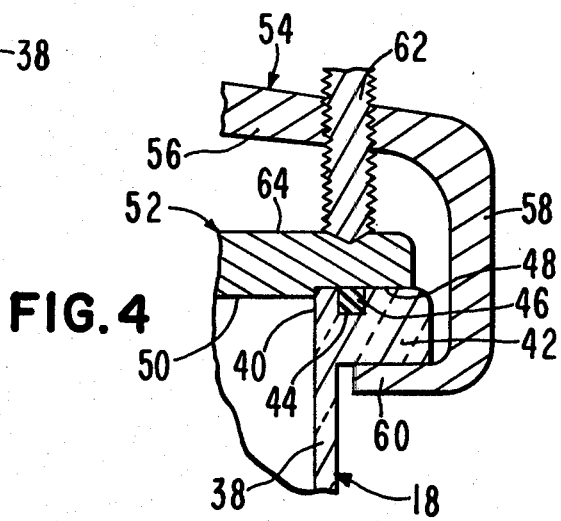
FIG. 4 is an enlarged fragmentary cross-sectional view of the jar and lid, showing the way in which the lid is held firmly to the jar in closing relationship to the open top of the jar.

Lid 52 is releasably held onto the jar in any suitable manner, such as by a removable clamp 54 having a central part 56 (FIG. 4) and a pair of parallel sides 58, each side 58 having a lateral end projection 60 for underlying and engaging flange 42 in the manner shown in FIG. 4. A pair of set screws 62 are threaded into central part 56 near respective ends thereof and bear on the upper surface 64 of lid 52 to thereby urge the lid into closing relationship to top 40 of jar 18. The clamp, when in use, is centrally located with respect to the diameter of the jar as shown in FIG. 2.

Figure 3:
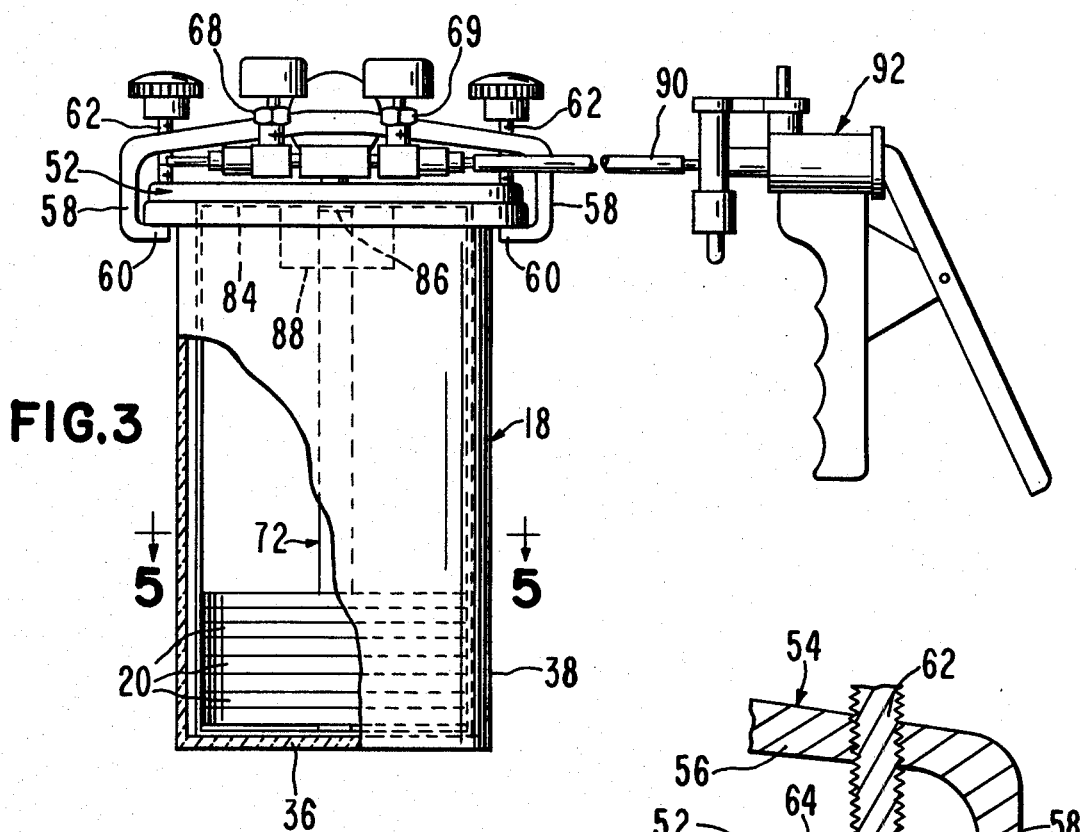
FIG. 3 is a side elevational view of the incubator jar for insertion in the housing of the apparatus, with the jar having a lid sealed to the upper open end thereof and with a hand-actuated suction pump coupled to the air outlet orifice of the top.

Lid 54 also carries a conduit 66 having a pair of valves 68 and 69 on opposite sides of an orifice 73 which places conduit 66 in fluid communication with the interior of jar 18 when lid 52 is in its operative position on the jar as shown in FIGS. 3 and 4. Knobs 70 are used to open and close valves 68. One valve is used to control air flow out of the jar and the other valve is used to control gas flow into the jar.

Figure 5:
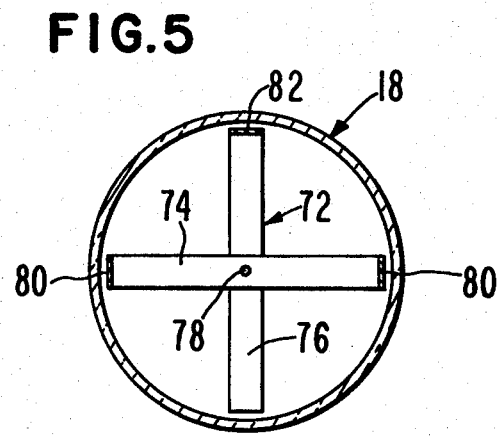
FIG. 5 is a cross-sectional view taken along line 5—5 of FIG. 3.

A culture dish holder 72 (FIGS. 3 and 5), is provided in jar 18. Holder 72 includes a pair of bottom members 74 and 76 which are joined together at a location 78, such as by spot welding. A pair of vertical members 80 extend upwardly from the the ends of member 74 and a vertical member 82 extends upwardly from one end of member 76. The opposite end of member 76 is free of any such vertical member, so that culture dishes 20 can be moved laterally onto the holder. At the top of holder 72, a first cross member 84 interconnects the upper ends of member 80 and a second member 86 is secured to the upper end of member 82, members 84 and 86 being secured together where they cross, such as by spot welding. Strap means 88 carried in any suitable manner by members 84 and 86 provide a recess for receiving a perforated box (not shown) of small size containing an oxygen absorber in the event that oxygen is to be eliminated from jar 18. Culture dishes 20 are stacked by inserting them into the open side of holder 72.

In use, the various culture dishes 20 to be used are stacked in holder 72 in the manner shown in FIG. 3. Then the holder is placed within jar 18 and lid 52 is placed on the jar, following which clamp 54 is put in place and screws 62 manipulated until the lid is sealed to the jar. Then, a hose 90 is connected to one end of conduit 66 and also connected to the air inlet end of a hand actuated vacuum pump 92. Valves 69 is open while valve 68 is closed, following which pump 92 is actuated to draw air by suction out of jar 18 to at least partially evacuate the same. During this time, heater coils 26, or heater 35 if cylinder 31 is used, is actuated to generate heat within housing 12 which will affect the cultures in culture dishes 20.

When the desired vacuum is achieved, valve 69 is closed and a suitable gas can be injected into the opposite end 96 of conduit 66 by opening valve 68. A gas can be supplied to jar 18 to a negative pressure of, for instance, 5 psi, following which valve 68 is then closed so that the desired environment will have been then created. The above process can be repeated several times to eliminate all of the oxygen in the jar. Then, the jar is left in the housing 12 for a certain period of time such as the desired incubation period and then the jar can be removed and the culture dishes removed from the jar for inspection and testing.

Incubation apparatus 10 is adapted to be operated at all times with negative pressure in jar 18. Due to this feature, it is possible to take a specimen from surgery, immediately place it on a dish 20, and then immediately place the dish in jar 18, and hand pump the interior of the jar to a negative pressure. The jar can then be sent with the specimen in it to a lab for evaluation. This produces the shortest possible exposure to the atmosphere. The vacuum in the jar will hold most cultures for 12 hours or more without gas injection which will be used in the final incubation culture.

Thus, a most important feature is the time element involved in getting the specimen out of the atmospheric oxygen into the rare oxygen vacuum of jar 18. The jar can be pumped down to a negative pressure in a matter of minutes with the hand pump. The speed with which a specimen can be isolated is a most important factor in evaluating it.

A pressure gauge 71 can be carried by lid 52 to indicate gas pressures, positive or negative, within the jar. A typical pump suitable for use as pump 92 is one known as MityVac manufactured and sold by Neward Enterprises, Cucamonga, Calif.

I claim:

1. A portable incubator comprising: a jar having an open top and a bottom; a holder for a number of stackable culture dishes, the holder being inserted into the jar through the open top thereof and supported on the bottom of the jar; a lid; means releasably mounting the lid on the jar in sealing relationship to the open top thereof; a conduit having a pair of opposed, open ends, there being a valve adjacent each end of the conduit, respectively, for controlling the flow of fluid therethrough, said conduit coupled with the lid and having means intermediate the ends placing it in fluid communication with the jar when the lid is mounted thereon; and a hand-actuated suction pump having means for coupling the same to one end of the conduit, the pump being positionable adjacent to the jar and capable of being carried therewith.

2. A portable incubator as set forth in claim 1, wherein is included a substantially closed housing having a top with an opening, the jar being insertable in the housing through the top opening thereof and into a position below the top opening with the upper part of the jar engaging the top, and a heater means in the housing for heating the contents of the jar when the latter is in said position.

3. A portable incubator as set forth in claim 2, wherein said housing is a box-like structure provided with a top wall, said top opening being in the top wall, said structure having sidewall means spaced laterally from the operative position of the jar, said heater means being on the inner surface of the sidewall means.

4. A portable incubator as set forth in claim 2, wherein said housing includes an open top cylinder of heat conducting material, the heater means being on the outer surface of the cylinder.

5. A portable incubator set forth in claim 1, wherein the mounting means comprises a clamp; said conduit being generally horizontal when the lid is on the jar and being adjacent to the outer periphery of the lid.

6. A portable incubator as set forth in claim 1, wherein the pump has an air inlet end, and including a flexible tube connecting one end of the conduit with said inlet end of said vacuum pump.

7. A portable incubator as set forth in claim 1, wherein said holder has an open side for receiving the culture dishes, and a bottom for supporting the culture dishes received thereby.

8. A portable incubator as set forth in claim 7, wherein the holder includes a pair of spaced opposed, rigid, generally vertical members having a first rigid strap for interconnecting the upper ends of the members and a second rigid strap for interconnecting the lower ends, and a third rigid, generally vertical member spaced from and disposed out of the plane of said pair of members.

9. A portable incubator as set forth in claim 7, wherein there is included means defining a recess on the upper end of the holder for retaining an oxygen absorber.

10. A portable incubator as set forth in claim 1, wherein the jar has an upper, annular groove, and a quad seal flange in the groove for sealingly engaging a lower, outer peripheral surface of the lid.

11. A portable incubator as set forth in claim 1, wherein is included a housing having a top wall provided with an opening for receiving the jar, the jar having a flange engageable with the top wall for limiting the inward movement of the jar into the housing, the latter having a sidewall spaced from the jar when the jar is in the housing, and heater means in the housing for heating the contents of the jar when the latter is in said housing.

12. A portable incubator as set forth in claim 11, wherein there is included a cylinder of heat conductive carried by the top wall and extending downwardly therefrom with the cylinder having an open top vertically aligned with the opening in the top wall, a cylinder adapted to receive the jar, said heating means including a heater coil surrounding the cylinder.

13. A portable incubator comprising: a substantially closed housing having a top wall provided with an opening therethrough; a jar having an open top and an annular flange surrounding the open top, the jar being inserted into the housing through the opening thereof and moved into a position below the opening with the top of the jar near the opening, the flange being engageable with the top wall for supporting the jar in said position; said flange having a groove in the upper surface thereof; a quad seal in the groove; a lid movable into covering relationship with the top of the jar and having an outer peripheral lower face engageable with the seal for sealing the junction between the flange and the lid, the lid having a hole therethrough; a conduit having a pair of opposed, open ends; a valve for each end of the conduit, respectively, each valve being coupled to the conduit to control the flow of fluid through the respective conduit end, the valves being on opposite sides of the hole, said conduit coupled with the lid and having means intermediate the ends placing it in fluid communication with the jar when the lid is mounted thereon; a clamp removably carried by the lid and operable to couple the lid to the jar with the outer peripheral lower face of the lid in sealing engagement with said quad seal; a hand-held, hand-actuated suction pump having an air inlet end; a flexible tube removably connecting the inlet end of the vacuum pump with one end of the conduit, whereby the jar can be evacutated when the lid is secured to the jar and when the valve near the opposite end of the conduit is closed and the valve corresponding to said one end of said conduit is open; and heater means in the housing for heating the contents of the jar when the latter is in said operative position.

14. A portable incubator as set forth in claim 13, wherein said heater means comprises a heater coil on the inner surface of the housing.

15. A portable incubator unit as set forth in claim 13, wherein is included a cylinder secured to the top wall and extending downwardly therefrom, the cylinder having an open top aligned with the opening in the top wall, the jar adapted to be inserted into the cylinder, said heater means comprising a heater coil surrounding the cylinder and in heat exchange relationship thereto.

16. In a portable incubator unit having an open top jar provided with a circular flange surrounding the open top thereof, a lid for covering the jar, the lid having a generally flat lower surface, there being a conduit above the upper surface of the lid and the lid having a hole therethrough; means on the lid for placing the hole and thereby the interior of the jar in fluid communication with the conduit at a location thereon intermediate its ends; means coupled with the top for securing the same to the flange of the jar; and means for sealing the junction between said flat lower surface of the lid and the flange when the lid covers the jar.

* * * * *